(12) United States Patent
Ziemer et al.

(10) Patent No.: US 9,198,996 B2
(45) Date of Patent: Dec. 1, 2015

(54) WATER-ABSORBING COMPOSITES

(75) Inventors: Antje Ziemer, Mannheim (DE); Horst Kaluza, Ludwigshafen (DE); Ernst Jürgen Bauer, Ludwigshafen (DE); Stefan Bruhns, Hellerup (DK); Thomas Daniel, Waldsee (DE); John Christian Schmitt, Cologne (DE); Kerstin Meyer-Lipp, Bad Nauheim (DE); Guenter Reinhard Schmidt, Linden (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/117,380

(22) PCT Filed: May 15, 2012

(86) PCT No.: PCT/EP2012/058965
§ 371 (c)(1),
(2), (4) Date: Nov. 13, 2013

(87) PCT Pub. No.: WO2012/156385
PCT Pub. Date: Nov. 22, 2012

(65) Prior Publication Data
US 2014/0158626 A1  Jun. 12, 2014

Related U.S. Application Data

(60) Provisional application No. 61/487,302, filed on May 18, 2011.

(51) Int. Cl.
| | |
|---|---|
| *B01J 20/22* | (2006.01) |
| *A61L 15/60* | (2006.01) |
| *A61L 15/42* | (2006.01) |
| *B32B 5/24* | (2006.01) |
| *B01D 15/00* | (2006.01) |
| *A61F 13/53* | (2006.01) |

(52) U.S. Cl.
CPC .............. *A61L 15/60* (2013.01); *A61L 15/425* (2013.01); *B01D 15/00* (2013.01); *B32B 5/245* (2013.01); *A61F 2013/530649* (2013.01); *B32B 2262/02* (2013.01); *B32B 2262/0276* (2013.01); *B32B 2266/0242* (2013.01); *B32B 2307/726* (2013.01); *B32B 2307/728* (2013.01); *B32B 2555/00* (2013.01)

(58) Field of Classification Search
CPC ................................. B01J 20/22; B01J 20/26
USPC .......................................... 502/401, 402, 526
See application file for complete search history.

(56) References Cited

U.S. PATENT DOCUMENTS

| | | | |
|---|---|---|---|
| 6,136,873 | A | 10/2000 | Hahnle et al. |
| 6,174,929 | B1 | 1/2001 | Hahnle et al. |
| 6,455,600 | B1 | 9/2002 | Hahnle et al. |
| 6,750,262 | B1 | 6/2004 | Hahnle et al. |
| 7,867,623 | B2 | 1/2011 | Ziemer et al. |
| 7,923,479 | B2 | 4/2011 | Champ et al. |
| 2008/0215026 | A1 | 9/2008 | Schornick et al. |
| 2009/0045138 | A1 | 2/2009 | Champ et al. |

FOREIGN PATENT DOCUMENTS

| | | |
|---|---|---|
| DE | 10 34 90 60 A1 | 10/2004 |
| EP | 858 478 A1 | 8/1998 |
| GB | 2 467 554 A | 8/2010 |
| WO | WO-97/31971 A1 | 9/1997 |
| WO | WO-99/44648 A1 | 9/1999 |
| WO | WO-00/52087 A1 | 9/2000 |
| WO | WO-03/066717 A2 | 8/2003 |
| WO | WO-2004/007598 A1 | 1/2004 |
| WO | WO-2004/035668 A2 | 4/2004 |
| WO | WO-2005/042039 A2 | 5/2005 |
| WO | WO-2006/094977 A2 | 9/2006 |

OTHER PUBLICATIONS

International Search Report in international application No. PCT/EP2012/058965, dated Jul. 20, 2012.

*Primary Examiner* — Edward Johnson
(74) *Attorney, Agent, or Firm* — Marshall, Gerstein & Borun LLP

(57) ABSTRACT

This invention relates to a process for producing water-absorbing composites comprising the steps of foaming an aqueous mixture comprising at least one monoethylenically unsaturated monomer bearing acid groups, at least one crosslinker, at least one initiator and at least one surfactant, contacting the foam obtained with at least one web of synthetic fibers and polymerizing, to the composites themselves and to their use for absorbing aqueous fluids.

15 Claims, No Drawings

WATER-ABSORBING COMPOSITES

CROSS-REFERENCE TO RELATED APPLICATIONS

This is the U.S. national phase of International Application No. PCT/EP2012/058965, filed May 15, 2012, which claims the benefit of U.S. provisional application No. 61/487,302, filed May 18, 2011, incorporated herein by reference in its entirety.

This invention relates to a process for producing water-absorbing composites comprising the steps of foaming an aqueous mixture comprising at least one monoethylenically unsaturated monomer bearing acid groups, at least one crosslinker, at least one initiator and at least one surfactant, contacting the foam obtained with a web and polymerizing, to the composites themselves and to their use for absorbing aqueous fluids.

Further embodiments of the present invention are discernible from the claims, the description and the examples. It will be appreciated that the hereinabove identified and the hereinbelow still to be more particularly described features of the subject matter of the present invention are utilizable not just in the particular combination indicated but also in other combinations without leaving the realm of the present invention.

Water-absorbing foams based on crosslinked monomers comprising acid groups are known, cf. EP 858 478 B1, WO 97/31971 A1, WO 99/44648 A1 and WO 00/52087 A1. They are produced for example by foaming a polymerizable aqueous mixture comprising not less than 50 mol % neutralized acid-functional monoethylenically unsaturated monomers, crosslinkers and at least one surfactant and then polymerizing the foamed mixture. The foaming of the polymerizable mixture can be effected for example by dispersing fine bubbles of a gas which is inert toward free radicals or by dissolving such a gas in the polymerizable mixture under elevated pressure and depressurizing the mixture. The water content of the foams is set in the range from 1% to 60% by weight for example. The foams may be subjected to surface-postcrosslinking, if appropriate, by spraying a crosslinker onto the foamed material or dipping the foam into the crosslinker and heating the crosslinker-laden foam to a higher temperature. The foams are used for example in hygiene articles to acquire, distribute and store body fluids.

WO 03/066717 A2 discloses a process whereby wet strength is enhanced and residual monomer content lowered for superabsorbent foams by addition of amino-comprising polymers.

WO 2004/007598 A1 discloses water-absorbing foams comprising finely divided hydrophilic silicon dioxide and/or a surfactant at the surface. The treatment of the foams leads to an increase in the takeup rate for liquids.

WO 2004/035668 A2 discloses water-absorbing foams comprising superabsorbent fibers or fruit fibers, in particular apple fibers.

WO 2006/094977 A2 describes water-absorbing foams comprising wood fibers or waste paper fibers.

WO 2005/042 039 A2 describes hydrogels possessing enhanced blood absorbence due to their being coated with hydrophobic compounds.

The present invention has for its object to improve the properties of water-absorbing foams, in particular to provide foams that have good absorbing, retaining and conducting properties for aqueous fluids and are stable, in particular in the wet state, efficiently handleable, efficiently processable and simple to produce.

The present invention further has for its object to provide water-absorbing foams which swell one-dimensionally only and which do not shrink on drying.

We have found that this object is achieved by water-absorbing composites comprising at least one water-absorbing foam layer and at least one web layer, the web composed of synthetic fiber and having a basis weight of not more than 200 $g/m^2$ and a thickness of not more than 5 mm.

Water-absorbing foams are known from the prior art. Water-absorbing foam herein refers to a foam which has a centrifuge retention capacity (CRC, method of measurement described hereinbelow in the "Methods of determination" section) of at least 3 g/g, preferably at least 4 g/g, more preferably at least 5 g/g and especially at least 6 g/g.

Water-absorbing composites are conveniently obtainable by foaming an aqueous mixture comprising at least one monoethylenic unsaturated monomer bearing acid groups, the monomer being optionally at least partially neutralized, at least one crosslinker and at least one surfactant and also optionally additives or auxiliaries, such as solubilizers, thickeners, stabilizers, fillers, fibers and/or cell nucleators, contacting the resulting foam with a web, and polymerizing.

One embodiment of the present invention comprises foaming an aqueous mixture comprising for example a) 10% to 95% by weight of monoethylenically unsaturated monomers which comprise acid groups and are at least 10 mol % neutralized, b) optionally in addition up to 50% by weight of other monoethylenically unsaturated monomers, c) 0.001% to 20% by weight of crosslinker, d) initiators, e) 0.01% to 20% by weight of at least one surfactant, f) optionally a solubilizer and g) optionally thickeners, foam stabilizers, polymerization regulators, fillers, fibers and/or cell nucleators, all based on the total amount of the mixture. This aqueous polymerizable mixture may also be called "monomer mixture" or "monomer solution".

The foaming of the aqueous mixtures can be effected for example by dispersing in the mixture fine bubbles of a gas which is inert toward free radicals, or by dissolving such a gas in the polymerizable mixture at a pressure in the range from 2 to 400 bar and subsequently decompressing the mixture to atmospheric. This provides a flowable foam which can be filled into molds or cured on a belt. Curing is effected by addition polymerization.

Suitable monomers a) are for example ethylenically unsaturated carboxylic acids, such as acrylic acid, methacrylic acid, maleic acid, fumaric acid and itaconic acid. Acrylic acid and methacrylic acid are particularly preferred monomers. Acrylic acid is most preferable.

The proportion of acrylic acid and/or salts thereof in the total amount of monomers a) is preferably at least 50 mol %, more preferably at least 90 mol %, most preferably at least 95 mol %.

The monomers a) and especially acrylic acid comprise preferably up to 0.025% by weight of a hydroquinone half ether. Preferred hydroquinone half ethers are hydroquinone monomethyl ether (MEHQ) and/or tocopherols.

Tocopherol refers to compounds of the following formula:

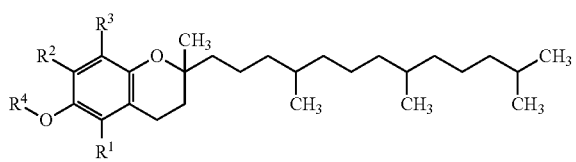

where R¹ is hydrogen or methyl, R² is hydrogen or methyl, R³ is hydrogen or methyl and R⁴ is hydrogen or an acid radical of 1 to 20 carbon atoms.

Preferred R⁴ radicals are acetyl, ascorbyl, succinyl, nicotinyl and other physiologically tolerable carboxylic acids. The carboxylic acids can be mono-, di- or tricarboxylic acids.

Preference is given to alpha-tocopherol where R¹=R²=R³=methyl, especially racemic alpha-tocopherol. R⁴ is more preferably hydrogen or acetyl. RRR-alpha-Tocopherol is preferred in particular.

The monomer solution comprises generally up to about 200 ppm, preferably not more than 130 weight ppm, more preferably not more than 70 weight ppm, preferably not less than 10 weight ppm, more preferably not less than 30 weight ppm and especially about 50 weight ppm of hydroquinone half ether, all based on acrylic acid, with acrylic acid salts being arithmetically counted as acrylic acid. For example, the monomer solution can be produced using an acrylic acid having an appropriate hydroquinone half ether content.

The acid groups of the monomers a) have typically been neutralized to an extent of 25 to 95 mol %, preferably to an extent of 40 to 85 mol %, more preferably to an extent of 50 to 80 mol %, especially preferably to an extent of 55 to 75 mol %, for which the customary neutralizing agents can be used, examples being alkali metal hydroxides, alkali metal oxides, alkali metal carbonates or alkali metal bicarbonates and also mixtures thereof.

Neutralization can also be effected with ammonia, amines or alkanolamines, such as ethanolamine, diethanolamine or triethanolamine, however. Preferred neutralizing agents are tertiary alkanolamines, such as triethanolamine, methyldiethanolamine, dimethylaminodiglycol, dimethylethanolamine and N,N,N',N'-tetra(hydroxyethyl)ethylenediamine. The preferred neutralizing agents can also be used in admixture with further neutralizing agents.

In a preferred embodiment of the present invention, 10 to 90 mol %, preferably 20 to 80 mol %, more preferably 30 to 70 mol %, most preferably 40 to 60 mol %, of the neutralized monomers a) have been neutralized by means of an alkanolamine.

With a rising proportion of alkanolamine, both the flexibility of the polymeric foams and the extractables content increase.

The amount of monomer a) is preferably 20 to 90% by weight, more preferably 30 to 85% by weight, most preferably 35 to 75% by weight, based in each case on the unneutralized monomer a) and on the monomer solution or suspension. Based on the unneutralized monomer a) means in the context of this invention that the proportion of the monomer a) before the neutralization is used for the calculation, i.e. the contribution of the neutralization is not taken into account.

Monomers b) are ethylenically unsaturated monomers that are copolymerizable with the monomers a), examples being acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Crosslinkers c) are compounds having at least two polymerizable groups which can be free-radically interpolymerized into the polymer network. Useful crosslinkers c) include for example ethylene glycol dimethacrylate, diethylene glycol diacrylate, allyl methacrylate, trimethylolpropane triacrylate, triallylamine, tetraallyloxyethane as described in EP 530 438 A1, di- and triacrylates as described in EP 547 847 A1, EP 559 476 A1, EP 632 068 A1, WO 93/21237 A1, WO 03/104299 A1, WO 03/104300 A1, WO 03/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures as described for example in DE 195 43 368 A1, DE 196 46 484 A1, WO 90/15830 A1 and WO 02/32962 A2.

Useful crosslinkers c) include in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate, ethylene glycol dimethacrylate and also trimethylolpropane triacrylate and allyl compounds, such as allyl (meth)acrylate, triallyl cyanurate, diallyl maleate, polyallyl esters, tetraallyloxyethane, triallylamine, tetraallylethylenediamine, allyl esters of phosphoric acid and also vinylphosphonic acid derivatives as described for example in EP 343 427 A2. Useful crosslinkers c) further include pentaerythritol diallyl ether, pentaerythritol triallyl ether, pentaerythritol tetraallyl ether, polyethylene glycol diallyl ether, ethylene glycol diallyl ether, glycerol diallyl ether, glycerol triallyl ether, polyallyl ethers based on sorbitol, and also ethoxylated variants thereof. The process of the present invention may utilize di(meth)acrylates of polyethylene glycols, the polyethylene glycol used having a molecular weight between 300 and 1000.

However, particularly advantageous crosslinkers c) are di- and triacrylates of 3- to 20-tuply ethoxylated glycerol, of 3- to 20-tuply ethoxylated trimethylolpropane, of 3- to 20-tuply ethoxylated trimethylolethane, especially di- and triacrylates of 2- to 6-tuply ethoxylated glycerol or of 2- to 6-tuply ethoxylated trimethylolpropane, of 3-tuply propoxylated glycerol, of 3-tuply propoxylated trimethylolpropane, and also of 3-tuply mixedly ethoxylated or propoxylated glycerol, of 3-tuply mixedly ethoxylated or propoxylated trimethylolpropane, of 15-tuply ethoxylated glycerol, of 15-tuply ethoxylated trimethylolpropane, of at least 40-tuply ethoxylated glycerol, of at least 40-tuply ethoxylated trimethylolethane and also of at least 40-tuply ethoxylated trimethylolpropane.

Very particularly preferred for use as crosslinkers c) are diacrylated, dimethacrylated, triacrylated or trimethacrylated multiply ethoxylated and/or propoxylated glycerols as described for example in WO 03/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. The triacrylates of 3- to 5-tuply ethoxylated and/or propoxylated glycerol are most preferred.

The amount of crosslinker c) is preferably 0.5 to 15% by weight, more preferably 2 to 10% by weight and most preferably 3 to 8% by weight, based in each case on the unneutralized monomer a). With rising crosslinker content, the centrifuge retention capacity (CRC) falls and the absorption capacity under a pressure typically passes through a maximum.

Useful initiators d) for the polymerization reaction include all compounds that disintegrate into free radicals under the polymerization conditions, examples being peroxides, hydroperoxides, hydrogen peroxide, persulfates, azo compounds and the so-called redox catalysts, and also any other known method for generating free radicals, examples being high energy radiation, such as UV light for example. The use of water-soluble initiators or UV light is preferred. It is advantageous in some cases to use mixtures of various polymerization initiators, examples being mixtures of hydrogen peroxide and sodium or potassium peroxodisulfate. Mixtures of hydrogen peroxide and sodium peroxodisulfate can be used in any desired ratio. Suitable organic peroxides are for example acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di-(2-ethylhexyl) peroxidicarbonate, dicyclohexyl peroxidicarbonate, di-(4-tert-butylcyclohexyl) peroxidicarbonate, dimyristil peroxidicarbonate, diacetyl peroxidicarbonate, allyl peresters, cumyl peroxyneodecanoate, tert-butyl per-3,5,5-trimethylhexanoate, acetylcyclohexylsulfonyl peroxide, dilauryl peroxide, dibenzoyl peroxide and tert-amyl perneodecanoate. Particularly suitable polymerization initiators d) are azo initiators, for example 2,2'-azobis(2-amidinopropane)dihydrochloride, 2,2'-azobis(N,N-dimethylene)isobutylramidine dihydrochloride, 2-(carbamoylazo)isobutyronitrile, 2,2'-azobis[2-(2'-imidazolin-2-yl)propane]dihydrochloride and 4,4'-azobis (4-cyanovaleric acid). The polymerization initiators mentioned are used in customary amounts, generally at least 0.01 mol %, preferably at least 0.05 mol % and also more preferably at least 1 mol % and also generally not more than 5 mol % and preferably not more than 2 mol %, based on the monomers to be polymerized.

The redox catalysts comprise, as oxidizing component, at least one of the above-indicated per compounds and, as reducing component, for example ascorbic acid, glucose, sorbose, ammonium bisulfite, ammonium sulfite, ammonium thiosulfate, ammonium hyposulfite, ammonium pyrosulfite, ammonium sulfide, alkali metal bisulfite, alkali metal sulfite, alkali metal thiosulfate, alkali metal hyposulfite, alkali metal pyrosulfite, alkali metal sulfide, metal salts, such as iron(II) ions or silver ions or sodium hydroxymethylsulfoxylate. The reducing component of the redox catalyst is preferably ascorbic acid, sodium sulfite or sodium pyrosulfite. Generally from $3 \cdot 10^{-6}$ mol % and preferably at least $1 \cdot 10^{-5}$ to 1 mol % of the reducing component of the redox initiator and generally at least $1 \cdot 10^{-5}$ mol % and preferably at least $1 \cdot 10^{-3}$ to 5 mol % of the oxidizing component are used based on the amount of monomers used in the polymerization. Instead of the oxidizing component or in addition it is also possible to use one or more water-soluble azo initiators.

One embodiment of the present invention utilizes a redox initiator consisting of hydrogen peroxide, sodium peroxodisulfate and ascorbic acid. These components are used for example in the concentrations of $1 \cdot 10^{-2}$ mol % of hydrogen peroxide, 0.084 mol % of sodium peroxodisulfate and $2.5 \cdot 10^{-3}$ mol % of ascorbic acid, based on the monomers.

However, the polymerization can also be started in the absence of initiators of the abovementioned kind through the action of high energy radiation in the presence of photoinitiators. These may be for example what are known as α-splitters, H-radiating systems or else azides. Examples of such initiators are benzophenone derivatives such as Michler's ketone, phenanthrene derivatives, fluorene derivatives, anthraquinone derivatives, thioxanthone derivatives, coumarin derivatives, benzoin ethers and derivatives thereof, azo compounds such as the free-radical formers mentioned above, substituted hexaarylbisimidazoles or acylphosphine oxides. Examples of azides are: 2-(N,N-dimethylamino)ethyl 4-azidocinnamate, 2-(N,N-dimethylamino)ethyl 4-azidonaphthyl ketone, 2-(N,N-dimethylamino)ethyl 4-azidobenzoate, 5-azido-1-naphthyl 2'-(N,N-dimethylamino)ethyl sulfone, N-(4-sulfonylazidophenyl)maleimide, N-acetyl-4-sulfonylazidoaniline, 4-sulfonylazidoaniline, 4-azidoaniline, 4-azidophenacyl bromide, p-azidobenzoic acid, 2,6-bis(p-azidobenzylidene)cyclohexanone and 2,6-bis(p-azidobenzylidene)-4-methylcyclohexanone. Photoinitiators, if used, are typically used in amounts from 0.001% to 5% by weight preferably 0.001 to 2% by weight, more preferably 0.01 to 1% by weight, most preferably 0.05 to 0.2% by weight, based in each case on the unneutralized monomer a) to be polymerized.

The aqueous monomer solution may comprise the initiator in dissolved or dispersed form. However, the initiators may also be added to the polymerization reactor separately from the monomer solution.

The polymerizable aqueous mixtures comprise at least one surfactant e) as a further component. The surfactants e) are of decisive importance for forming and stabilizing the foam. It is possible to use anionic, cationic or nonionic surfactants or surfactant mixtures which are compatible with each other. It is possible to use low molecular weight or else polymeric surfactants, and combinations of different or else similar types of surfactants have been determined to be advantageous. Examples of nonionic surfactants are addition products of alkylene oxides, especially ethylene oxide, propylene oxide and/or butylene oxide, with alcohols, amines, phenols, naphthols or carboxylic acids. The surfactants used are advantageously addition products of ethylene oxide and/or propylene oxide with alcohols comprising at least 10 carbon atoms, the addition products comprising from 3 to 200 mol of ethylene oxide and/or propylene oxide per mole of alcohol. The alkylene oxide units are present in the addition products in the form of blocks or in random distribution. Examples of useful nonionic surfactants are the addition products of 7 mol of ethylene oxide with 1 mol of tallow fat alcohol, reaction products of 9 mol of ethylene oxide with 1 mol of tallow fat alcohol and addition products of 80 mol of ethylene oxide with 1 mol of tallow fat alcohol. Further useful commercially available nonionic surfactants comprise reaction products of oxo process alcohols or Ziegler alcohols with from 5 to 12 mol of ethylene oxide per mole of alcohol, especially with 7 mol of ethylene oxide. Further useful commercially available nonionic surfactants are obtained by ethoxylation of castor oil. The amount of ethylene oxide added per mole of castor oil is for example in the range from 12 to 80 mol. Further useful commercially available products are for example the reaction products of 18 mol of ethylene oxide with 1 mol of tallow fat alcohol, the addition products of 10 mol of ethylene oxide with 1 mol of a $C_{13}/C_{15}$ oxo process alcohol or the reaction products of from 7 to 8 mol of ethylene oxide with 1 mol of a $C_{13}/C_{15}$ oxo process alcohol. Useful nonionic surfactants further include phenol alkoxylates such as for example p-tert-butylphenol which has been reacted with 9 mol of ethylene oxide or methyl ethers of reaction products of 1 mol of a $C_{12}$-$C_{18}$ alcohol and 7.5 mol of ethylene oxide.

The nonionic surfactants described above, for example by esterification with sulfuric acid, can be converted into the corresponding acid sulfuric esters. The acid sulfuric esters are used in the form of their alkali metal or ammonium salts as anionic surfactants. Useful anionic surfactants include for example alkali metal or ammonium salts of acid sulfuric esters of addition products of ethylene oxide and/or propylene oxide with fatty alcohols, alkali metal or ammonium salts of alkylbenzenesulfonic acid or of alkylphenol ether sulfates. Products of the kind mentioned are commercially available. For example, the sodium salt of an acid sulfuric ester of a $C_{13}/C_{15}$ oxo process alcohol reacted with 106 mol of ethylene oxide, the triethanolamine salt of dodecylbenzenesulfonic acid, the sodium salt of alkylphenol ether sulfates and the sodium salt of the acid sulfuric ester of a reaction product of 106 mol of ethylene oxide with 1 mol of tallow fat alcohol are useful commercially available anionic surfactants. Useful anionic surfactants further include acid sulfuric esters of $C_{13}/C_{15}$ oxo process alcohols, paraffinsulfonic acids such as Cis-alkylsulfonate, alkyl-substituted benzenesulfonic acids and alkyl-substituted naphthalenesulfonic acids such as dodecylbenzenesulfonic acid and di-n-butylnaphthalenesulfonic acid and also fatty alcohol phosphates such as $C_{15}/C_{18}$ fatty alcohol phosphate. The polymerizable aqueous mixture can comprise combinations of a nonionic surfactant and an anionic surfactant or combinations of nonionic surfactants or combinations of anionic surfactants. Even cationic surfactants are suitable. Examples thereof are the dimethyl sulfate quaternized reaction products of 6.5 mol of ethylene oxide with 1 mol of oleylamine, distearyldimethylammonium chloride, lauryltrimethylammonium chloride, cetylpyridinium bromide and dimethyl sulfate quaternized triethanolamine stearate, which is preferably used as a cationic surfactant.

The amount of surfactant, based on the unneutralized monomer a) is preferably 0.01 to 10% by weight, more preferably 0.1 to 6% by weight, most preferably 0.8 to 3% by weight.

The polymerizable aqueous mixtures may optionally comprise at least one solubilizer f) as a further component. Solubilizers are water-miscible organic solvents, for example dimethyl sulfoxide, dimethylformamide, N-methylpyrrolidone, monohydric alcohols, glycols, polyethylene glycols or monoethers derived therefrom, subject to the proviso that the monoethers do not comprise any double bonds in the molecule. Useful ethers include methylglycol, butylglycol, butyldiglycol, methyldiglycol, butyltriglycol, 3-ethoxy-1-propanol and glycerol monomethyl ether.

When solubilizers f) are used, they are preferably included in the aqueous mixture at up to 50% by weight, more preferably in the range from 1% to 25% by weight and most preferably in the range from 5% to 10% by weight.

The aqueous mixture may optionally comprise thickeners, foam stabilizers, fillers, fibers and/or cell nucleators g). Thickeners are used for example to optimize foam structure and to improve foam stability. As a result, the foam will shrink only minimally during the polymerization. Useful thickeners include all natural and synthetic polymers known for this purpose that substantially increase the viscosity of an aqueous system and do not react with the amino groups of the basic polymers. The synthetic and natural polymers in question can be swellable or soluble in water. An exhaustive overview of thickeners may be found for example in the publications by R. Y. Lochhead and W. R. Fron, Cosmetics & Toiletries, 108, 95-135 (May 1993) and M. T. Clarke, "Rheological Additives" in D. Laba (ed.) "Rheological Properties of Cosmetics and Toiletries", Cosmetic Science and Technology Series, Vol. 13, Marcel Dekker Inc., New York 1993.

Water-swellable or water-soluble synthetic polymers useful as thickeners include for example high molecular weight polyethylene glycols or copolymers of ethylene glycol and propylene glycol and also high molecular weight polysaccharides such as starch, guar flour, locust bean flour or derivatives of natural substances such as carboxymethylcellulose, hydroxyethylcellulose, hydroxymethylcellulose, hydroxypropylcellulose and mixed cellulose ethers. A further group of thickeners are water-insoluble products, such as finely divided silica, zeolites, bentonite, cellulose powders and other finely divided powders of crosslinked polymers. The aqueous mixtures may comprise the thickeners in amounts up to 30% by weight. When such thickeners are used at all, they are included in the aqueous mixture in amounts of 0.1%, preferably 0.5% up to 20% by weight.

To optimize foam structure, the aqueous reaction mixture may be admixed, if appropriate, with hydrocarbons having at least 5 carbon atoms in the molecule. Useful hydrocarbons include for example pentane, cyclopentane, hexane, cyclohexane, heptane, octane, isooctane, decane and dodecane. The contemplated aliphatic hydrocarbons can be straight-chain, branched or cyclic and have a boiling temperature which is above the temperature of the aqueous mixture during foaming. The aliphatic hydrocarbons extend the pot life of the foamed aqueous reaction mixture which has not yet polymerized. This facilitates the handling of the foams which have not yet polymerized and increases process consistency. The hydrocarbons act for example as cell nucleators and also stabilize the foam which has already formed. In addition, they can effect a further foaming of the mixture in the course of the polymerization of the monomer foam. They can then also have the function of a blowing agent. Instead of hydrocarbons or in a mixture therewith, it is also possible to use optionally chlorinated or fluorinated hydrocarbons as a cell nucleator and/or foam stabilizer, for example dichloromethane, trichloromethane, 1,2-dichloroethane, trichlorofluoromethane or 1,1,2-trichlorotrifluoroethane. When hydrocarbons are used, they are used for example in amounts from 0.1% to 20% by weight and preferably from 0.1% to 10% by weight, based on the polymerizable aqueous mixture.

To modify the properties of the foams, the polymerizable aqueous mixture may have added to it one or more fillers, for example chalk, talc, clay, titanium dioxide, magnesium oxide, aluminum oxide, precipitated silicas in hydrophilic or hydrophobic forms, dolomite and/or calcium sulfate. The particle size of the fillers is for example in the range from 10 to 1000 µm and preferably in the range from 50 to 850 µm. The fillers can be included in the polymerizable aqueous mixture in amounts up to 30% by weight.

The aqueous mixtures described above, which comprise the monomers a), crosslinker c), initiator d) and surfactant e) as mandatory components, are initially foamed. For example, an inert gas can be dissolved in the polymerizable aqueous mixture at a pressure of for example 2-400 bar and the mixture subsequently decompressed to atmospheric. Decompression from a nozzle produces a flowable foam. The polymerizable aqueous mixture can also be foamed by another method, namely by dispersing fine bubbles of an inert gas in the polymerizable aqueous mixture. The foaming of the polymerizable aqueous mixture on a laboratory scale can be effected for example by foaming the aqueous mixture in a kitchen processor equipped with a whisk. Foaming is preferably carried out in an inert gas atmosphere and with inert gases, for example by mixing with nitrogen or noble gases under atmospheric or superatmospheric pressure, for example up to 25 bar, followed by decompression. The consistency of the foams, the size of the gas bubbles and the distribution of the gas bubbles in the foam can be varied within wide limits, for example through the choice of surfactants e), solubilizers f), foam stabilizers, cell nucleators, thickeners and fillers g). As a result, the density, the open-cell content of the foam and the wall thickness of the foam are readily adjustable to specific values. The aqueous mixture is preferably foamed at temperatures which are below the boiling point of the constituents of the aqueous mixture, for example in the range from room temperature to 100° C. and preferably in the range from 20 to 50° C. However, the aqueous mixture can also be foamed at temperatures above the boiling point of the component having the lowest boiling point by foaming the mixture in a pressuretightly sealed container. Foamed mixtures are obtained which are flowable and stable for a prolonged period. The density of the foamed mixture is for example in the range from 0.01 to 0.9 g/cm$^3$ at 20° C.

In the second stage of the process, the foamed mixture is contacted with a web. For example, to produce a superabsorbent foam sheet or roll-good, the foamed mixture is spread on the web by usual means, such as a blade-coater or a slit nozzle used for foaming by decompression. The desired thickness of the foam can easily be set in this step.

Webs are nonwoven articles of manufacture which are composed of fibers and whose integrity is generally due to the intrinsic clingingness of the fibers. Webs are preferably consolidated mechanically, for example by needling, interlooping or entangling by means of sharp jets of water or air. Webs can also be consolidated adhesively or cohesively. Adhesively consolidated webs are obtainable for example by interadhering the fibers with liquid binders or by melting binder fibers which are added to the web in the course of its production. Cohesively consolidated webs are producible for example by incipiently dissolving the fibers with suitable chemicals and applying pressure.

Examples of synthetic fibers are fibers composed of polyethylene, polypropylene, polybutylene terephthalate, polyamide, polyethylene terephthalate, polyester, polysulfone and/or polyether ketone. It is also possible to use fibers composed of carbon or glass fibers. Polyester webs are particularly preferred.

The basis weight of the webs is preferably not more than 150 g/m$^2$, more preferably in the range from 5 to 100 g/m$^2$ and most preferably in the range from 8 to 40 g/m$^2$.

The thickness of the webs is preferably in the range from 0.01 to 4 mm, more preferably in the range from 0.01 to 1 mm and most preferably in the range from 0.05 to 0.5 mm.

Either the monomer foam can be added to a web previously placed on a suitable support, or a web can be placed on a monomer foam previously applied to a suitable support. But it is also possible first to apply a portion of the monomer foam to a suitable support, place the web on top and subsequently add the rest of the monomer foam. For example, the foam can be knifecoated onto the support in the desired thickness. The support has advantageously been provided with an antistick coating.

The amount of monomer foam and the web may be chosen such that the monomer foam is completely penetrated by the web, i.e., the monomer foam preferably extends to less than 20% beyond the web, more preferably to less than 10% and most preferably to less than 5%, all based on the total thickness of the foam. This enhances the stability of the present invention's composites in the swollen state. Alternatively, the amount of monomer foam and the web may be chosen such that the web is completely penetrated by the monomer foam, i.e., the monomer foam has an integral web support.

To create multi-layered structures that may be desired for certain applications, it is also possible to use two webs, i.e., to put a second web on monomer foam that has been added to a first web, to create a layer of foam between to webs. A second web may also be added to the web/foam structure after polymerizing the monomer foam or after any subsequent processing step. Analogously, multiple-layer composites may be created by adding more foam and web layers. In such composites having more than one foam or web layer, the individual foam and web layers may be chemically or structurally identical or different.

In the third stage of the process, the monomers are polymerized in the presence of the web. The polymerization is carried out in the presence of customary radical-forming initiators. This gives crosslinked polymers which are superabsorbent. The radicals can be generated for example by heating (thermal polymerization) or by irradiation with light of a suitable wavelength (UV polymerization).

Inventive composites having a layer thickness of up to about 5 millimeters are produced for example by unilateral or bilateral heating or in particular by unilateral or bilateral irradiation of the foamed polymerized or polymerizable aqueous mixture. When thicker composites are to be produced, for example composites several centimeters in thickness, it is particularly advantageous to heat the foamed material by means of microwaves, since relatively uniform heating can be achieved in this way. In this case, the thermal polymerization is effected for example at temperatures in the range from 20 to 140° C., preferably in the range from 40° C. to 120° C., more preferably in the range from 60 to 110° C. and most preferably in the range from 80 to 100° C. In the case of thicker composites, the foamed mixture is heat-treated on both surfaces, for example using contact heating or by irradiation or in a drying cabinet. The polymeric foams are open celled. The open cell content is for example at least 80% and preferably above 90%. Particular preference is given to foams having an open cell content of 100%. The open cell content of a foam is determined using scanning electron microscopy for example.

After the polymerizing of the foamed mixture or during the polymerizing, the hydrogel foam is dried. This removes water and other volatile constituents from the crosslinked hydrogel foam. Examples of suitable drying processes are thermal convection drying such as forced air drying, thermal contact drying such as roll drying, radiation drying such as infrared drying, dielectric drying such as microwave drying and freeze drying. The drying temperatures are typically in the range of 50 to 200° C., preferably 60 to 150° C., more preferably 80 to 120° C., most preferably 90 to 110° C. The preferred residence time at this temperature in the drier is preferably at least 1 minute, more preferably at least 2 minutes, most preferably at least 5 minutes, and typically at most 20 minutes. In order to avoid undesired decomposition and crosslinking reactions, it may be advantageous to perform the drying under reduced pressure, under a protective gas atmosphere and/or under gentle thermal conditions, under which the product temperature does not exceed 120° C., preferably 100° C. A particularly suitable drying process is (vacuum) belt drying.

Individual or all drying steps in the process of this invention are preferably carried out at reduced pressure, i.e. a pressure below atmospheric pressure, preferably at less than 500 mbar and more preferably at less than 200 mbar, and are optionally augmented by means of a dry stream of gas, preferably nitrogen, at a rate in the range from 20 to 1000 l/kgh and preferably in the range from 100 to 250 l/kgh, based on the mass of product to be dried.

After the drying step, the composite will usually comprise less than 10% by weight of water. However, the water content of the composite can be adjusted to any desired value by moistening with liquid water or water vapor. The water content of the composite is usually in the range from 1% to 60% by weight and preferably in the range from 2% to 10% by weight. The water content can be used to adjust the flexibility of the composite. Completely dried composites are harsh and brittle, whereas foamed materials having a water content of 5-20% by weight for example are flexible.

Using the webs to be used in the process of the present invention provides water-absorbing composites which, on contact with water or aqueous fluids, will now only swell one-dimensionally, i.e., swelling takes the form of a change in the thickness and not the area of the composites.

The composites produced in accordance with the process of the present invention are notable compared with the hitherto customary water-absorbing foams in that they do not shrink on drying and in that they are mechanically stable.

In a preferred embodiment of the present invention, the composite properties are enhanced through the formation of complexes on the surface. Complexes are formed on the composite by treating with at least one complexing agent. A complexing agent is an agent that comprises complexing cations. Preferably, this is effected by spraying with solutions of bi- or more highly valent cations, the cations being capable of reacting with functional groups, for example the acid groups, of the polymeric foam to form complexes. Examples of bi- or more highly valent cations are polymers that, formally, are wholly or partly constructed from vinylamine monomers, such as partially or fully hydrolyzed polyvinylamide (so-called "polyvinylamine"), whose amine groups are always—even at very high pH values—partly present in a state of protonation to ammonium groups, or metal cations, such as $Mg^{2+}$, $Ca^{2+}$, $Al^{3+}$, $Sc^{3+}$, $Ti^{4+}$, $Mn^{2+}$, $Fe^{2+/3+}$, $Co^{2+}$, $Ni^{2+}$, $Cu^{2+}$, $Zn^{2+}$, $Y^{3+}$, $Zr^{4+}$, $La^{3+}$, $Ce^{4+}$, $Hf^{4+}$ and $Au^{3+}$. Preferred metal cations are $Mg^{2+}$, $Ca^{2+}$, $Al^{3+}$, $Ti^{4+}$, $Zr^{4+}$ and $La^{3+}$, and particularly preferred metal cations are $Al^{3+}$, $Ti^{4+}$ and $Zr^{4+}$. The metal cations can be used not only alone but also in admixture with each other. The anions are not subject to any fundamental restriction; of the metal cations mentioned, all metal salts that possess sufficient solubility in the solvent to be used are suitable. Metal salts with weakly complexing anions, for example chloride, nitrate and sulfate, bisulfate, carbonate, bicarbonate, nitrogen, phosphate, hydrogenphosphate, dihydrogenphosphate and carboxylate, such as acetate and lactate, are particularly suitable. It is particularly preferred to use aluminum sulfate $Al_2(SO_4)_3$. Useful solvents for the metal salts include water, alcohols, dimethylformamide, dimethyl sulfoxide and also mixtures thereof. Particular preference is given to water and water/alcohol mixtures, such as water/methanol, water/1,2-propanediol and water/1,3-propanediol. Water is very particularly preferred.

The concentration of the multivalent metal ion in the aqueous solution is generally at least 1% by weight, preferably at least 2% by weight and also generally not more than 20% by weight and preferably not more than 10% by weight. The amount of the multivalent metal ion used is generally at least 0.05% by weight, preferably at least 0.1% by weight and more preferably at least 0.2% by weight, for example at least 0.8% by weight, and also generally not more than 10% by weight, preferably not more than 8% by weight and more preferably not more than 5% by weight, for example not more than 3.2% by weight, based on the dry composite prior to application of the complexing agent. A composite is "dry" for the purposes of this invention when its water content is not more than 5% by weight. When aluminum sulfate is used, a cation content of 0.8% by weight corresponds to an $Al_2(SO_4)_3$ content of 5% by weight and a cation content of 3.2% by weight corresponds to an $Al_2(SO_4)_3$ content of 20% by weight.

The complexing agents to be applied are applied to the composite as described, preferably as a solution or, if insoluble, as a dispersion or solid.

The surface complexing step is optionally followed by drying. Drying can be effected in a conventional manner, say by heating the shell of the reaction apparatus or by blowing hot air into the reaction apparatus. It is similarly possible to use a downstream dryer as also used to dry the unaftertreated composite. Preferred drying temperatures range from 50 to 250° C., preferably from 50 to 200° C. and more preferably from 50 to 150° C. The residence time at this temperature in the dryer is advantageously below 30 minutes and preferably below 20 minutes.

The composites of the present invention may optionally be surface postcrosslinked. Post-crosslinkers suitable for this purpose are compounds that comprise at least two groups that are capable of forming covalent bonds with the carboxylate groups of the composite. Useful compounds include for example alkoxysilyl compounds, polyaziridines, polyamines, polyamidoamines, di- or polyepoxides, as described in EP 83 022 A2, EP 543 303 A1 and EP 937 736 A2, di- or polyfunctional alcohols, as described in DE 33 14 019 A1, DE 35 23 617 A1 and EP 450 922 A2, or R-hydroxyalkylamides, as described in DE 102 04 938 A1 and U.S. Pat. No. 6,239,230.

Postcrosslinking is typically carried out by spraying the composite with a solution of the postcrosslinker. But it is also possible to dip the composite into a solution of the post-crosslinker. Subsequently, the composite is thermally dried, and the crosslinking reaction can take place not only before but also during drying. The drying temperatures are typically in the range of 100 to 250° C., preferably 120 to 220° C., more preferably 130 to 210° C., most preferably 150 to 200° C. The preferred residence time at this temperature in the drier is preferably at least 10 minutes, more preferably at least 20 minutes, most preferably at least 30 minutes, and typically at most 60 minutes. In order to avoid undesired decomposition and crosslinking reactions, it may be advantageous to perform the drying under reduced pressure, under a protective gas atmosphere and/or under gentle thermal conditions, under which the product temperature does not exceed 120° C., preferably 100° C. A particularly suitable drying process is (vacuum) belt drying.

To improve the properties, the composites, in particular the foam part of them, can additionally be coated or remoisturized, or other additives may be added.

Suitable coatings for improving the speed of liquids absorption and the liquids permeability in the foam are, for example, inorganic inert substances, such as water-insoluble metal salts, organic polymers, cationic polymers and di- or polyvalent metal cations, such as aluminum sulfate and aluminum lactate. Suitable coatings for counteracting the undesired caking tendency are, for example, fumed silica, such as Aerosil® 200, and surfactants, such as Span® 20.

Suitable additives for reducing the content of unconverted monomers (residual monomers) are, for example, reducing agents such as the salts of sulfurous acid, of hypophosphorous acid and/or of organic sulfinic acid. Preferable reducing agents are sodium disulfite ($Na_2S_2O_5$) or a mixture of the sodium salt of 2-hydroxy-2-sulfinatoacetic acid, the disodium salt of 2-hydroxy-2-sulfonatoacetic acid and sodium hydrogensulfite. Such mixtures are available as Brüggolite® FF6 and Brüggolite® FF7 (Brüggemann Chemicals; Heilbronn; Germany). If used, these reducing agents are typically added in amounts of at least 0.01% by weight, preferably at least 0.5% by weight and more preferably at least 1% by weight and of not more than 5% by weight, preferably not more than 4% by weight and more preferably not more than 3% by weight, based on the weight of dry foam. 2 to 2.5% by weight of sodium disulfite, for example 2.25% by weight, will provide sufficient residual monomer reduction in most cases. These additives may be added at any suitable stage in the process, for example during or after the surface complexing, surface crosslinking or additional coating steps.

The thickness of the foam in the composite of this invention, in a form suitable for most purposes, is typically in the range from 0.05 to 4 mm, preferably in the range from 0.25 to 2.5 mm, more preferably in the range from 0.5 to 1.5 mm and most preferably in the range from 0.6 to 0.9 mm.

The optionally surface-postcrosslinked composite of the present invention can be used for all the purposes which for example the water-absorbing hydrogel foams which are known from EP 858 478 B1 and which are based on polymers comprising acid groups, such as on crosslinked polyacrylates. The composites of the present invention are useful for example in hygiene articles for absorbing body fluids, in dressing material for covering wounds, as a sealing material, as a packaging material, as a soil improver, as a soil substitute, for dewatering sludges, for absorbing acidic aqueous wastes, for thickening waterborne paints or coatings as part of the disposal of residual quantities thereof, for dewatering water-containing oils or hydrocarbons or as a material for filters in ventilation systems.

The present invention further provides articles for absorbing an aqueous fluid which comprise a water-absorbing composite in accordance with the present invention, such as baby diapers, sanitary napkins, incontinence articles and bandaging material.

Methods:

Measurements should unless otherwise stated be carried out at an ambient temperature of 23±2° C. and a relative humidity of 50±10%.

Free Swell Capacity (FSC)

The free swell capacity of the water-absorbing composite is determined as per DIN ISO 17190-5.

Centrifuge Retention Capacity (CRC)

The centrifuge retention capacity of the water-absorbing composite is determined as per DIN ISO 17190-6.

EXAMPLES

Examples 1 to 4

A magnetic stirrer was used to mix the following components together in a glass beaker:
209.13 g of acrylic acid
81.31 g of 37.3% sodium acrylate solution in water
16.8 g of polyethylene glycol diacrylate 400
25.60 g of 15% aqueous solution of an addition product of 80 mol of ethylene oxide onto 1 mol of a linear saturated $C_{16}$-$C_{18}$ fatty alcohol
26.62 g of water This solution was gradually admixed with 240.54 g of triethanolamine with ice cooling, followed by allowing to cool to 15° C. The solution obtained was transferred into a pressure vessel and saturated therein with carbon dioxide at a pressure of 12 bar for 25 minutes by passing a 300 l/h carbon dioxide stream through the solution. Under pressure, 16 g of a 3% by weight aqueous solution of 2,2'-azobis(2-amidinopropane)dihydrochloride were added and subsequently carbon dioxide was passed through the reaction mixture for a further 5 minutes. The reaction mixture was then expressed at a pressure of 12 bar through a die 1.0 mm in diameter to form a free-flowing fine-cell foam.

A polyester web was placed on an A3 size glass plate having rims 3 mm high. The monomer foam obtained was applied to the polyester web, and was covered with a second glass plate. The foam sample was irradiated simultaneously from both sides with UV light for 4 minutes, from above with a UVASPOT 1000/T UV/VIS radiator from Dr. Hönle A G, Gräfelfing, Germany, from below with 2 UVASPOT 400/T UV/VIS radiators from the same manufacturer.

The foam layer obtained was dried in a vacuum drying cabinet at 80° C. and subsequently adjusted to a moisture content of 5% by weight by spraying with water.

| | |
|---|---|
| Solids content of reaction mixture: | 81.35% |
| Degree of neutralization: | 60 mol % |
| Monomer foam density: | 0.24 gcm$^{-3}$ |
| Foam structure: | homogeneous, fully open-cell, no skin |

The properties of the water-absorbing composite are reported in Table 1.

Example 5

The procedure of Examples 1 to 4 was repeated. Half the monomer foam was applied to the glass plate before the polyester web was put in place.

The properties of the water-absorbing composite are reported in Table 1.

TABLE 1

Analysis results

| Example | Polyester web | Basis weight of web | Thickness of web | FSC [g/g] | CRC [g/g] |
|---|---|---|---|---|---|
| 1 | Coatil 20/K | 86.5 g/m$^2$ | 1.1 mm | 12.2 | 5.3 |
| 2 | Sawaloom ® 6305 | 60 g/m$^2$ | 3.1 mm | 16.6 | 6.0 |
| 3 | Sawabond ® 4131 | 35 g/m$^2$ | 0.64 mm | 30 | 6.5 |
| 4 | Sawaloom ® 6309 | 170 g/m$^2$ | 2.6 mm | 11.5 | 4.6 |
| 5 | Coatil 20/K | 86.5 g/m$^2$ | 1.1 mm | 13.9 | 5.7 |

Coatil 20/K polyester web (Libeltex BVBA, Meulebeke, Belgium)
Sawaloom ® 6305 polyester web (Sandler AG, Schwarzenbach/Saale, Germany)
Sawabond ® 4131 polyester web (Sandler AG, Schwarzenbach/Saale, Germany)
Sawaloom ® 6309 polyester web (Sandler AG, Schwarzenbach/Saale, Germany)

We claim:

1. A water-absorbing composite comprising at least one water-absorbing foam layer and at least one web layer, the web composed of synthetic fiber and having a basis weight of not more than 200 g/m$^2$ and a thickness of not more than 5 mm,
wherein the synthetic fiber is selected from the group consisting of polyethylene, polypropylene, polybutylene, terephthalate, polyamide, polyethylene terephthalate, polyester, polysulfone, polyether ketone, carbon, and glass fibers.

2. The composite according to claim 1 wherein the foam is fully penetrated by the web.

3. The composite according to claim 1 wherein the web is completely penetrated by the foam.

4. The composite according to claim 1 wherein the foam comprises at least one polymerized monoethylenically unsaturated monomer bearing at least one acid group.

5. The composite according to claim 4 wherein the acid groups of the polymerized monoethylenically unsaturated monomer are at least partly in a neutralized state.

6. The composite according to claim 1 wherein the foam comprises at least one polymerized crosslinker.

7. The composite according to claim 1 wherein the web consists of polyester fibers.

8. The composite according to claim 1 wherein the web is mechanically and/or thermally consolidated.

9. The composite according to claim 1 wherein the foam is coated with at least one salt of a multivalent cation.

10. The composite according to claim 1 wherein the water content of the composite is adjusted to a value between 1% and 60% by weight.

11. An article comprising a composite according to claim 1.

12. The composite of claim 1 wherein the synthetic fiber is a polyester.

13. The composite of claim 1 wherein the synthetic fiber has a basis weight of not more than 150 g/m$^2$.

14. The composite of claim 1 wherein the synthetic fiber has a basis weight of 5 to 100 g/m$^2$.

15. The composite of claim 1 wherein the synthetic fiber has a basis weight of 8 to 40 g/m$^2$.

* * * * *